(12) United States Patent
Long et al.

(10) Patent No.: US 7,366,333 B2
(45) Date of Patent: Apr. 29, 2008

(54) METHOD AND APPARATUS FOR SELECTING REGIONS OF INTEREST IN OPTICAL IMAGING

(75) Inventors: William F. Long, Quebec (CA); Yves Bérubé-Lauzière, Sherbrooke (CA); Laura McIntosh, Saint-Laurent (CA)

(73) Assignee: ART, Advanced Research Technologies, Inc., Ville Saint-Laurent, Québec (CA)

( * ) Notice: Subject to any disclaimer, the term of this patent is extended or adjusted under 35 U.S.C. 154(b) by 863 days.

(21) Appl. No.: 10/624,902

(22) Filed: Jul. 23, 2003

(65) Prior Publication Data
US 2004/0131234 A1 Jul. 8, 2004

Related U.S. Application Data

(60) Provisional application No. 60/505,339, filed on Dec. 12, 2002.

(30) Foreign Application Priority Data
Nov. 11, 2002 (WO) .................. PCT/IB02/04697

(51) Int. Cl.
*G06K 9/00* (2006.01)
*G06K 9/36* (2006.01)
(52) U.S. Cl. ............. 382/128; 382/110; 382/291
(58) Field of Classification Search .......... 382/110, 382/128, 287, 291; 600/414, 415, 426; 356/620, 356/624, 399–401
See application file for complete search history.

(56) References Cited

U.S. PATENT DOCUMENTS

| | | | |
|---|---|---|---|
| 4,633,494 A * | 12/1986 | Klausz | 378/205 |
| 4,896,343 A * | 1/1990 | Saunders | 378/95 |
| 5,090,401 A * | 2/1992 | Schwieker | 601/4 |
| 5,315,630 A * | 5/1994 | Sturm et al. | 378/65 |
| 5,531,520 A * | 7/1996 | Grimson et al. | 382/131 |
| 5,727,554 A * | 3/1998 | Kalend et al. | 600/587 |
| 5,823,192 A * | 10/1998 | Kalend et al. | 128/845 |
| 5,894,615 A * | 4/1999 | Alexander | 5/421 |
| 6,396,940 B1* | 5/2002 | Carrott et al. | 382/128 |
| 6,405,072 B1 | 6/2002 | Cosman | 600/426 |
| 6,614,452 B1* | 9/2003 | Cable | 715/764 |
| 6,662,036 B2* | 12/2003 | Cosman | 600/411 |
| 6,833,915 B2* | 12/2004 | Beuthan et al. | 356/318 |
| 6,992,762 B2* | 1/2006 | Long et al. | 356/317 |
| 2002/0016533 A1 | 2/2002 | Marchitto et al. | 600/310 |
| 2002/0118280 A1* | 8/2002 | Medlar et al. | 348/77 |

FOREIGN PATENT DOCUMENTS

WO   WO 01/37195   * 5/2001

OTHER PUBLICATIONS

Hillman et al. Time Resolved Optical Tomography of the Human Forearm. Phys. Med. Biol. 46 (2001) 1117-1130.*
Pogue et al. Instrumentation and Design of a Frequency-Domain Diffuse Optical Tomography Imager for Breast Cancer Detection. Optics Express, vol. 1, No. 13 (1997) 391-403.*

* cited by examiner

*Primary Examiner*—Colin LaRose
(74) *Attorney, Agent, or Firm*—Bereskin & Parr

(57) ABSTRACT

There is provided a method and system for positioning a mammal for optical imaging in which a digital image of the mammal is obtained using a camera and a region of interest is selected using the digital image. The selected region is registered with an optical imaging system and the mammal is positioned in the imaging system to image the selected region of interest.

18 Claims, 2 Drawing Sheets

METHOD AND APPARATUS FOR SELECTING REGIONS OF INTEREST IN OPTICAL IMAGING

CROSS-REFERENCE TO RELATED APPLICATIONS

This application claims priority under 35USC§119(e) of U.S. patent application Ser. No. 10/317,857 filed Dec. 12, 2002 the petition to convert to a provisional patent application No. 60/505,339, filed Dec. 12, 2002 in accordance with 35USC§111(b)(6) and 37CFR1.53(c)(2) being filed concurrently herewith. This application is related to commonly assigned co-pending U.S. patent application No. 60/505,352 filed simultaneously herewith, the specification of which is hereby incorporated by reference.

TECHNICAL FIELD

The invention relates to the field of optical imaging and more specifically to the field of selecting regions of interest in a subject for optical imaging.

BACKGROUND OF THE INVENTION

Optical imaging has evolved to become a useful diagnostic tool. Various system designs have been developed to accommodate imaging of various parts of the human body. For example, Hillman et al. (Phys. Med. Biol, 46 (2001) 1117-1130) describes an arrangement for acquiring optical signals from a forearm; and Pogue et al. (Opt. Express 1 (1997) 391-403) describes a system for breast imaging. Optical imaging systems have also been developed for small mammals with a view of providing a research tool that can image changes in the physiology of the mammals and that can also provide information on the biodistribution molecules such as chromophores and fluorophores. An example of an optical imaging system for small mammals has been described in patent application WO 0137195.

Diagnosis as well as physiological and pharmacokinetics studies rely on time course protocols to reveal temporal changes within a subject with respect to predetermined characteristics. Thus, a suitable imaging tool should be able to reliably and reproducibly produce images of the same region of interest in a subject over time. In this respect accurate and reproducible positioning of the subject relative to the imaging optics is very important.

While the above mentioned optical imaging systems permit the repositioning of a subject in more or less the same position over several imaging sessions, they lack a positioning system that is reliable and precise. Thus there is a need for improved systems and methods for selecting regions of interest in a subject and reproducibly image the selected regions over time.

SUMMARY OF THE INVENTION

The present invention provides a system and method for selecting regions of interest (ROIs) in a subject such as a mammal and for reproducibly positioning the subject to image the same ROIs over time.

In one aspect of the invention there is provided a method for positioning a small mammal such as a mouse for optical imaging in which a digital image of the mammal is obtained and used to define a ROI by placing the mammal in the field of view of a camera. The ROI is then registered with an optical imaging system and the mammal is positioned relative to the imaging system in accordance with the coordinates of the ROI.

In an embodiment of the method, the ROI is selected by determining the contour of the ROI on a computer displayed image of a surface comprising the ROI.

In yet another aspect, a second digital image may be obtained to determine a plane at which the imaging system is focused for acquiring optical data when using an optical system in which light is propagated through air and wherein the optical signal is collected using lenses.

In yet another embodiment of the method, fiducial marks are inscribed on the subject and can be used as a reference for reproducible positioning of the subject and for selecting the same ROI over time.

In another aspect of the invention there is also provided a method for positioning a mammal for optical imaging which comprise determining a 3 Dimensional (3 D) contour of at least the part of the animal comprising the ROI and using the 3 D contour information in image reconstruction of the ROI.

The invention also provides a system for positioning a subject comprising a mammal supporting means, a camera for imaging a surface of the mammal comprising a ROI, storage means for storing the digital image, a display operationally linked to the storage means for displaying the stored digital image, a user interface to define the ROI, and a registering means for registering the defined ROI with an optical imaging system.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION OF THE PREFERRED EMBODIMENT

The present invention provides a system and method for selecting regions of interest (ROIs) for optical imaging in a subject such as a mammal and for reproducibly positioning the subject to image the same ROIs over time.

In accordance with one embodiment of the invention, a system for positioning a mammal or part thereof for optical imaging of a ROI of the mammal is provided, which allows the user to select a ROI of the mammal and register the coordinates of the selected region with an optical imaging system. This greatly facilitates manipulation of the mammal with a view of acquiring precise and reproducible optical images. In addition, the system in accordance with the invention permits the programming of the optical imaging system for automatic optical signal acquisition of the desired ROI. Furthermore, the coordinates of the ROI may be stored electronically for future retrieval and advantageously allowing the ROI to be repeatedly imaged over time, with a high degree of reproducibility. This characteristic enables time course experiments to be carried out on mammals by, for example, enabling pharmacokinetic studies, assessment of tumor growth and the like.

Figure 1:
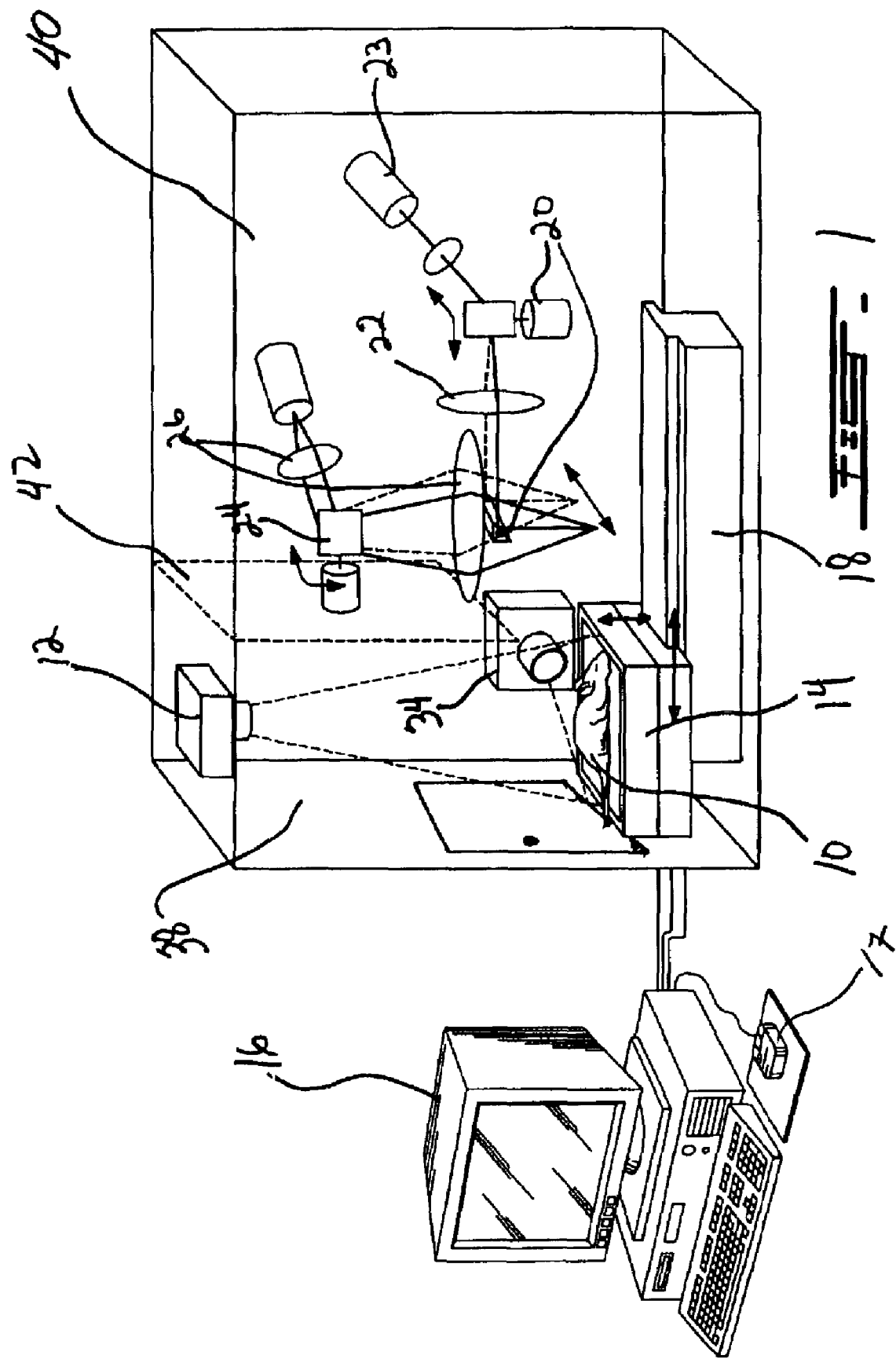
FIG. 1 is a perspective representation of an embodiment of an optical imaging system comprising a system for positioning a mammal in accordance with the invention.

FIG. 1 illustrates an embodiment of an optical imaging system comprising a system for positioning the mammal 10. In one embodiment, the system comprises a camera 12, a support 14 for the mammal, and a computer 16 operationally linked to the camera and the optical imaging system.

The mammal support is preferably a heated tray, and is preferably made of non-reflective substance, that can be moved relative to the optical imaging system. This can be achieved by providing a translation stage 18 on which the tray is mounted. In addition to the motion along the translational stage axis, the tray may also be moved up and down to place the animal in the object plane of the imaging optics. The computer may be coupled to the tray in order to provide the user with a means for remotely controlling the position of the tray. Preferably the animal is anesthetized to prevent it from moving during image acquisition. In this respect, the tray may comprise a mask and/or tubes coupled to an anesthetic supply to provide anesthetic to the animal while it is being imaged. The tray may also comprise a sensor in order to monitor animal movement during data acquisition. Advantageously the tray may also comprise physiological monitors such as electrocardiograph, temperature sensors, respiration monitors and the like.

The optical imaging system comprises a combination of mirrors 20 and lens 22 for directing the light source 23 onto the surface of the mammal, and a second set of mirror 24 and lenses 26 is provided for collecting and directing the light re-emitted from the mammal to a detector. The detector is in turn linked to the computer, where the acquired optical signals are processed for generating an image.

An embodiment of the method of the present invention is now described. First, a digital image of the surface of the mammal comprising the ROI is acquired by exposing the surface to the field of view of the camera 12. The digital image of the ROI permits the user to define the ROI and register the ROI with the optical imaging system as will be described below. Preferably the digital image is a live image and is continuously updated. Software instructions can then be used for proper positioning of the mammal relative to the optical imaging system in order to acquire the optical signals for image reconstruction. Acquisition of the image is preferably performed with the table at a predetermined position relative to the optical imaging system so as to provide an internal reference of coordinates.

Figure 2:
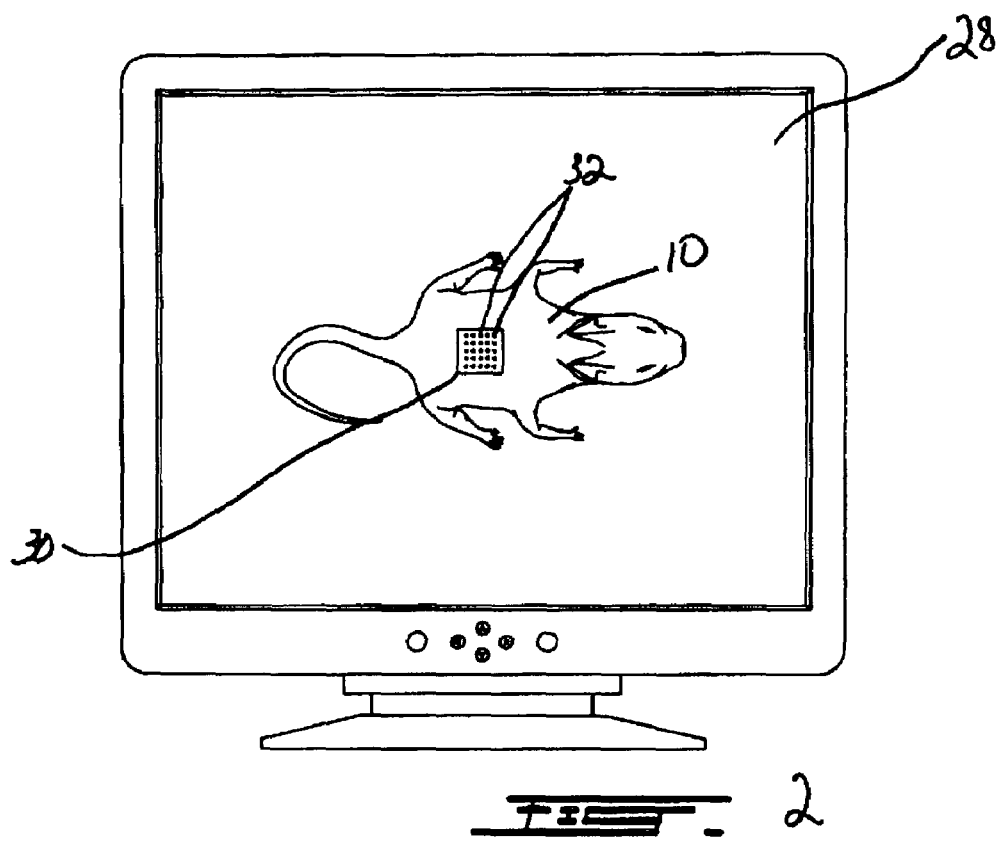
FIG. 2 is a computer display illustrating an embodiment of the selection of a region of interest.

Once the digital image has been acquired, the ROI may be defined by displaying the image of the surface comprising the ROI on a display screen 28 (FIG. 2). The user may then select the ROI 30 using a user interface drawing device, such as a mouse 17, for example. The selection of the ROI triggers the computer to digitally record the coordinates of the ROI. The coordinates may be stored in a memory for later retrieval.

The coordinates of the ROI are then used to program the optical imaging system to scan the region defined by the coordinates. This may be accomplished, for example, by programming the position of mirrors to direct the illumination beam and the optical signals re-emitted from the mammal to the appropriate location. In addition to defining the ROI, the user may also define the positions 32 within the ROI where the surface is to be illuminated by the beam of light, and the position where the optical signals re-emitted from the surface of the mammal are to be collected. Selection of illumination and detection points depends on the desired mode of optical imaging (continuous wave, time or frequency domain), the desired resolution, whether the image is topographic or tomographic and the like.

Figure 3:
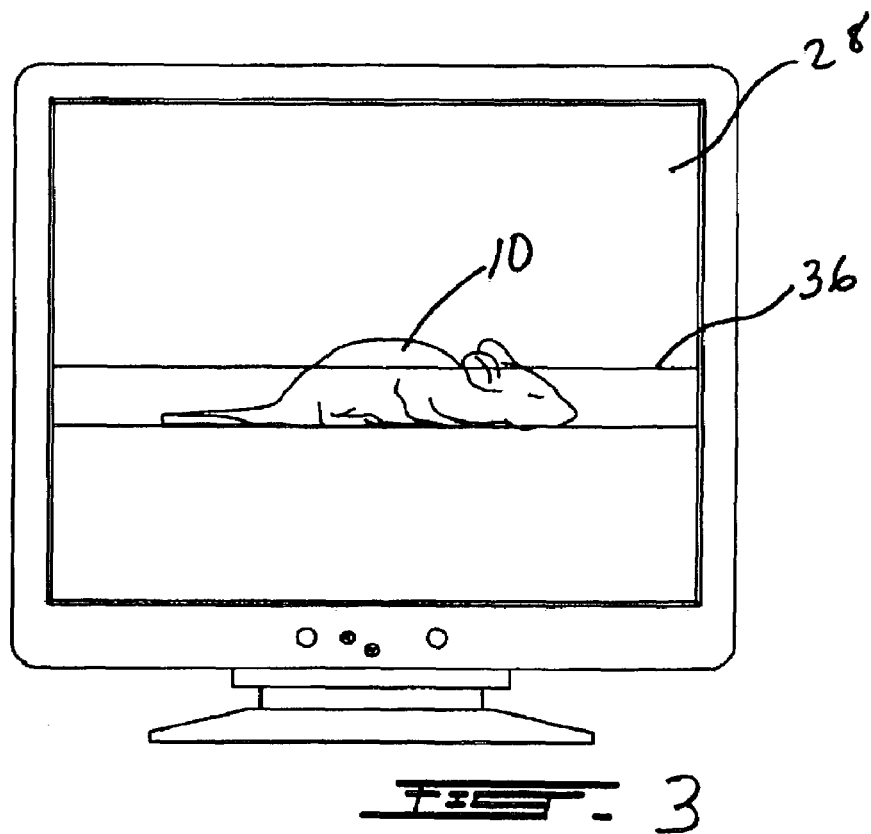
FIG. 3 is a computer display illustrating the selection of a plane of optical data acquisition according to an embodiment of the invention.

In a further embodiment, the system may also comprise a second camera 34 located on a side of the apparatus so as to provide a field of view that is substantially perpendicular to the field of view of the camera used to acquire the digital image of the surface comprising the ROI. In optical imaging systems in which the light is propagated through air (i.e. through free space optics) and wherein light re-emitted from the mammal is collected with lenses, the second camera allows the acquisition of a digital image that can be used to set the height of the mammal relative to the object plane 36 of the collection optics (FIG. 3). Accordingly, the image acquired by the first camera may be stored in the computer and displayed on a screen, overlaid with the live video image, thereby enabling the user to re-align the mammal in a particular plane prior to subsequent scans. As for the selection of the ROI, the plane of imaging may be selected using a user interface device, such as a mouse, for example.

The system may also comprise means to determine the volumetric profile of the animal. In one embodiment, the volumetric profile can be determined by scanning the animal with a laser beam directed substantially perpendicularly to the animal. By simultaneously acquiring an image of the laser beam at the surface of the animal with a video camera placed at an angle to the laser path, the volumetric profile may be determined. The animal may be scanned by moving the tray. It will be appreciated that the volumetric profile thus obtained provides spatial information useful for image reconstruction and display.

In a preferred embodiment, the cameras are located in a positioning chamber 38 optically insulated from the chamber 40 comprising the optical components by baffle 42. In this embodiment, the tray may be moved back and forth between the optical chamber and the positioning chamber by displacement on the translation stage which spans the two compartments. This permits the user to easily manipulate the mammal in the positioning chamber without interfering with or risking disturbing the various optical components.

In another embodiment, fiducial marks may be inscribed on the mammal to provide references that can be used to select the region of interest when a plurality of optical images are acquired over time so that the same region of interest is selected and registered with the optical system. The fiducial marks may also be used for registering the optical images with another imaging modality such as computed tomography (CT), magnetic resonance imaging (MRI) and the like.

The embodiment(s) of the invention described above is(are) intended to be exemplary only. The scope of the invention is therefore intended to be limited solely by the scope of the appended claims.

We claim:

1. A method for positioning a mammal or part thereof for diagnostic optical imaging, the method comprising:
   i) obtaining a digital image of a surface of the mammal comprising a region of interest (ROI);
   ii) defining the ROI;
   iii) registering coordinates of the ROI with a diagnostic optical imaging system having collection optics components; and
   iv) positioning the mammal in three dimensions relative to an object plane of the collection optics based on said registered coordinates of said ROI such as to locate the object plane at said surface of the mammal and image the ROI.

2. The method as claimed in claim 1, wherein the step of obtaining a digital image comprises:
   i) positioning the mammal on a support so as to expose the surface of the mammal comprising the ROI to a field of view of a camera; and
   ii) acquiring a digital image of the exposed surface.

3. The method as claimed in claim 2, wherein the step of defining the ROI comprises:
   i) displaying the image of the surface comprising the ROI on a display;
   ii) selecting the ROI to digitally record coordinates of the ROI; and
   iii) storing the digitalized coordinates of the ROI in a computer.

4. The method as claimed in claim 3, wherein the step of registering the ROI with a diagnostic optical imaging system comprises programming the optical imaging system to acquire optical data from the ROI defined by the digitalized coordinates.

5. The method as claimed in claim 4, further comprising the step of selecting a height of the mammal relative to the object plane of the collection optics at which the imaging system is focused for acquiring optical data.

6. The method as claimed in claim 5, wherein the step of selecting the height of the mammal comprises:
   i) obtaining a digital image of a surface of the mammal defined by a plane substantially perpendicular to the plane of the surface of the mammal comprising the ROI;
   ii) defining a plane corresponding to a desired object plane relative to the mammal at which the imaging system is focused;
   iii) digitally recording coordinates of the defined object plane;
   iv) storing the coordinates of the defined object plane;
   v) registering the coordinates of the object plane with the imaging system; and
   vi) positioning the mammal relative to the collecting optics such that the object plane comprises the ROI.

7. The method as claimed in claim 6 wherein a plurality of images of the ROI are obtained over time and wherein the stored coordinates of the defined plane and of the ROI are used for positioning the mammal at substantially the same position for each image.

8. The method as claimed in claim 7 wherein fiducial marks are inscribed on the surface of the mammal in the ROI to provide reference for positioning the mammal at substantially the same position for each image and for selecting substantially the same ROI.

9. A method for imaging a mammal or part thereof using a diagnostic optical imaging system having collection optics with an object plane, the method comprising:
   i) placing said mammal on a supporting means;
   ii) defining an ROI;
   iii) obtaining a three-dimensional (3 D) contour of said mammal comprising at least said ROI;
   iv) registering coordinates of said ROI and 3 D contour with the diagnostic optical imaging system;
   v) imaging said ROI of the mammal placed on said supporting means using said diagnostic optical imaging system wherein said coordinates of said 3 D contour are used in said generation of the image of said ROI, and in the positioning of the mammal or part thereof such that a surface of the mammal substantially coincides with the object plane of the collection optics.

10. The method as claimed in claim 9 wherein said step of obtaining a 3 D contour comprises:
    i) scanning said ROI with a laser beam directed substantially perpendicularly onto said ROI; and
    ii) simultaneously obtaining an image of said beam at said surface of the mammal.

11. A system for positioning a mammal for diagnostic optical imaging, the system comprising:
    i) a mammal support;
    ii) a camera for digitally imaging a surface of the mammal comprising a region of interest (ROI);
    iii) a storage element for storing the digital image;
    iv) a display operationally linked to the storage element for displaying the stored digital image;
    v) a user interface to define the ROI;
    vi) a registering element for registering the defined ROI with an optical imaging system; and
    vii) a positioning element for positioning the mammal in three dimensions relative to an object plane of the diagnostic imaging system so that said surface of the mammal coincides with said object plane for imaging of the ROI.

12. The system as claimed in claim 11, wherein the mammal supporting means is a tray.

13. The system as claimed in claim 12, wherein the tray is moveable relative to the optical imaging system.

14. The system as claimed in claim 13 wherein the tray comprises a motion sensor to detect movement of the mammal during imaging.

15. The system as claimed in claim 13 wherein the tray comprises one or more physiological sensor to monitor desired physiological states in the mammal.

16. The system as claimed in claim 12, wherein the tray is a heated tray.

17. The system as claimed in claim 12, wherein the system further comprises a second camera positioned such as to provide a field of view substantially perpendicular to the field of view of the first camera.

18. The system as claimed in claim 17 wherein the first and second camera, the mammal supporting means, the storage means, the display, the user interface and the registering means are operationally linked to a computer.

* * * * *